United States Patent
Janjic et al.

(10) Patent No.: US 6,670,132 B2
(45) Date of Patent: Dec. 30, 2003

(54) DETERMINING NON-NUCLEIC ACID MOLECULE BINDING TO TARGET BY COMPETITION WITH NUCLEIC ACID LIGAND

(75) Inventors: Nebojsa Janjic, Boulder, CO (US); Larry Gold, Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 10/021,330

(22) Filed: Dec. 10, 2001

(65) Prior Publication Data

US 2002/0197617 A1 Dec. 26, 2002

Related U.S. Application Data

(63) Continuation of application No. 09/246,461, filed on Feb. 9, 1999, now Pat. No. 6,329,145.

(51) Int. Cl.[7] .......................... C12Q 1/68; C12N 11/02; G01N 33/544; C07K 17/02; C07H 21/00
(52) U.S. Cl. .......................... 435/6; 435/177; 436/528; 530/402; 530/413; 530/812; 536/22.1
(58) Field of Search ..................... 435/6, 177; 436/528; 536/22.1, 23.1; 530/402, 413, 812

(56) References Cited

U.S. PATENT DOCUMENTS

| | | | |
|---|---|---|---|
| 5,580,737 A | 12/1996 | Polisky et al. .................. | 435/6 |
| 5,723,323 A | 3/1998 | Kauffman et al. .............. | 435/6 |
| 5,780,228 A | 7/1998 | Parma et al. ................... | 435/6 |
| 5,789,163 A | 8/1998 | Drolet et al. ................... | 435/6 |
| 6,329,145 B1 * | 12/2001 | Janjic et al. .................... | 435/6 |

FOREIGN PATENT DOCUMENTS

| | | |
|---|---|---|
| GB | 2 183 661 A | 6/1987 |
| WO | WO 89/06694 | 7/1989 |
| WO | WO 91/19813 | 12/1991 |
| WO | WO 92/14843 | 9/1992 |

OTHER PUBLICATIONS

Ellington & Szostak (1990) Abstracts of papers presented at the 1990 meeting on RNA Processing, Cold Spring Harbor Laboratory, Cold Spring Harbor, NY, p. 84.

Fox et al. (1998) Drug Discovery & Development (Supplement to R& D Magazine), pp. 32–37.

Joyce (1989) Gene 82:83.

Joyce & Inoue (1989) Nucleic Acids Research 17:711.

Kinzler & Vogelstein (1989) Nucleic Acids Research 17:3645.

Kramer et al. (1974) J. Mol. Biol. 89:719.

Levisohn & Spiegelman (1969) Proc. Natl. Acad. Sci. USA 63:805.

Levisohn & Spiegelman (1968) Proc. Natl. Acad. Sci. USA 60:866.

Oliphant et al. (1989) Mol. Cell. Biol. 9:2944.

Oliphant & Struhl (1988) Nucleic Acids Research 16:7673.

Oliphant & Struhl (1987) Methods in Enzymology 155:568.

Oliphant et al. (1986) Gene 44:177.

Robertson & Joyce (1990) Nature 344:467.

Szostak, "Structure and Activity of Ribozymes," in *Redesigning the Molecules of Life*, (S.A. Benner ed.) Springer–Verlag Berlin Heidelberg, pp. 87–113, (1988).

Thiesen & Bach (1990) Nucleic Acids Research 18:3203.

\* cited by examiner

*Primary Examiner*—David M. Naff
(74) *Attorney, Agent, or Firm*—Swanson & Bratschun LLC

(57) ABSTRACT

A competitive binding assay is used to determine whether a non-nucleic acid molecule from a library of non-nucleic acid molecules binds to a target. The non-nucleic acid molecule competes with a nucleic acid ligand for binding to the target which may be immobilized. Detecting displacement of nucleic acid ligand from a complex of the nucleic acid ligand and the target determines binding of the non-nucleic acid molecule to the target. The nucleic acid ligand may be immobilized and contacted with a target to form a complex. Adding a non-nucleic acid molecule to the complex displaces target from the complex, and detecting displacement of the target determines binding of the non-nucleic acid molecule to the target. Labeled nucleic acid ligand or labeled target displaced from or remaining in the complex can be detected for detecting displacement. Nucleic acid ligands that bind to the target are identified by the SELEX method. The assay provides a high throughput screening method for determining whether a non-nucleic acid molecule binds to a target.

12 Claims, 10 Drawing Sheets

| Competitor | Structure | $K_{dC}$, μM | EC50, μM |
|---|---|---|---|
| Evans Blue | 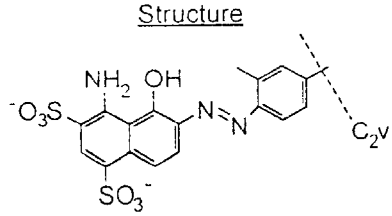 | 0.15 ± 0.04 | 5.6 |
| Trypan Blue | 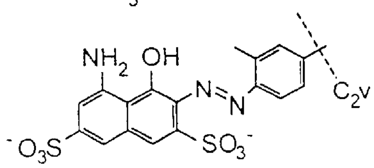 | 0.26 ± 0.06 | 6.1 |
| Suramin | 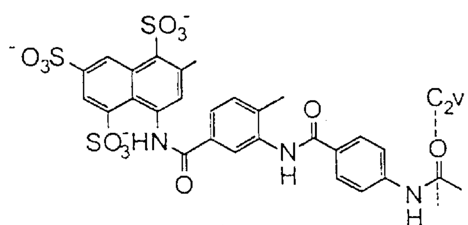 | 1.1 ± 0.4 | 57 |
| Calcion | 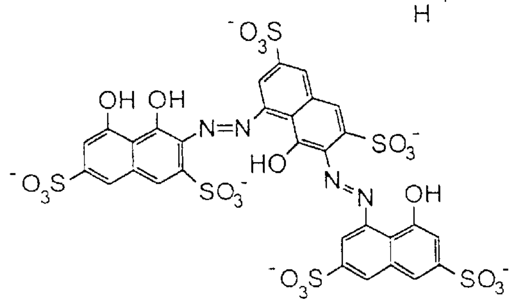 | 7.8 ± 1.2 | 280 |
| SPADNS | 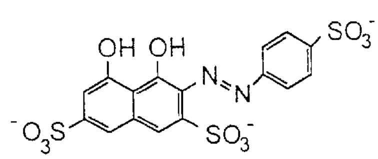 | 19 ± 6 | 100 |
| Azocarmine B | 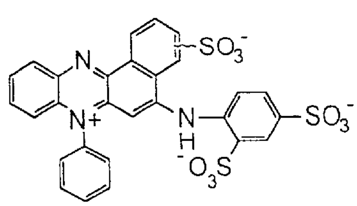 | 22 ± 3.0 | >1000 |

FIGURE 1A

| Competitor | Structure | $K_{dC}$, μM | EC50, μM |
|---|---|---|---|
| Amaranth | 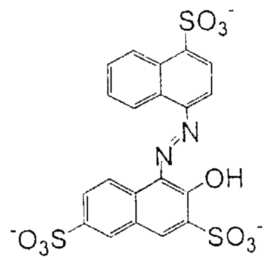 | 48 ± 16 | 510 |
| Sulfonazo III | 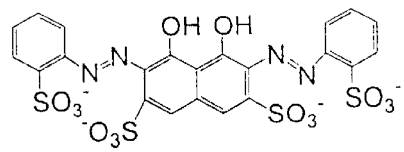 | 74 ± 27 | >1000 |
| New Coccine | 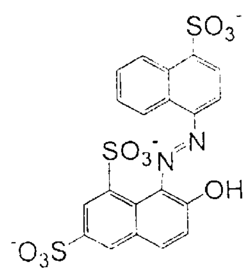 | 120 ± 20 | 930 |
| myoInositol hexasulfate | 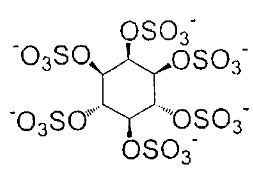 | 720 ± 200 | >1000 |
| Naphthalene 1,3,6-trisulfonic acid | 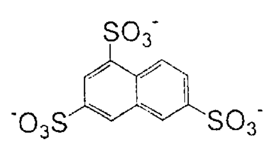 | 870 ± 400 | >1000 |
| Sucrose octasulfate | 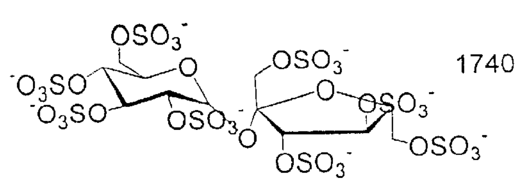 | 1740 ± 450 | >1000 |

FIGURE 1B

| Competitor | Structure | $K_{dC}$, μM | EC50, μM |
|---|---|---|---|
| PDGF Aptamer (20ta) | | 0.000050 ± 0.000055 | |
| PDGF Aptamer (20tb) | | 0.00039 ± 0.00016 | |
| PDGF Aptamer (PD 316) | | 0.000070 ± 0.000030 | 0.005 |
| VEGF Aptamer (31838SP) | | >1 | >1 |

FIGURE 1C

| Competitor | Structure | $K_{dC}, \mu M$ |
|---|---|---|
| GlcNAc | 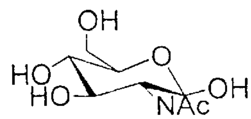 | >10000 |
| (GlcNAc)$_2$ | 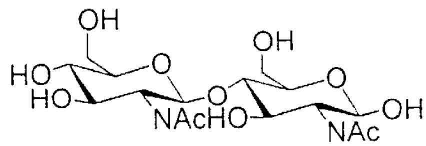 | 83 ± 21 |
| (GlcNAc)$_3$ | 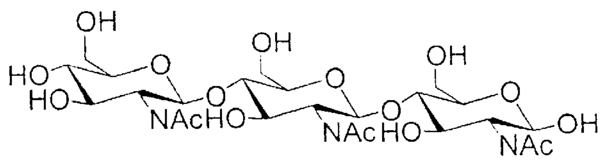 | 4 ± 0.3 |
| (GlcNAc)$_4$ | 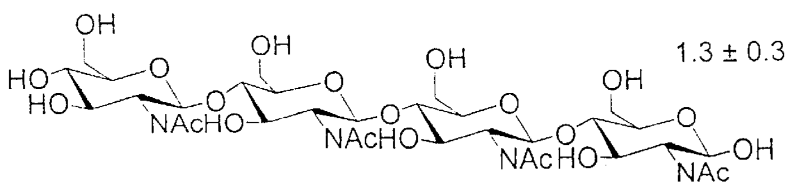 | 1.3 ± 0.3 |
| Fuc1-α-4GlcNAc | 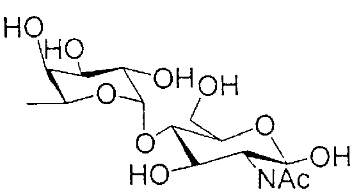 | 8100 ± 5200 |
| Fuc1-α-3GlcNAc | 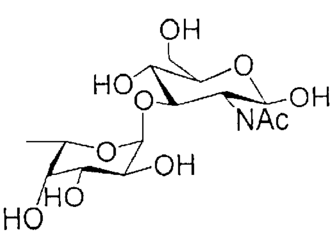 | 6600 ± 5300 |

FIGURE 3A

| Competitor | Structure | $K_{dC}$, µM |
|---|---|---|
| Lewis A trisaccharide {Gal1-B-3[Fuc1-α-4]GlcNAc} | 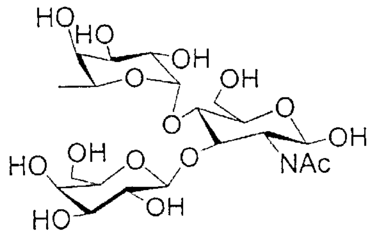 | 1500 ± 400 |
| Lewis X trisaccharide {Gal1-B-4[Fuc1-α-3]GlcNAc} | 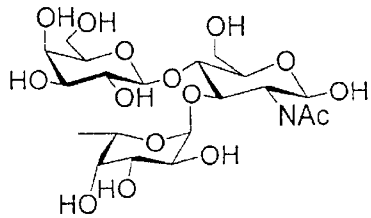 | 2600 ± 1400 |
| Lewis Y tetrasaccharide {Fuc1-α-2Gal1-B-4[Fuc1-α-3]GlcNAc} | 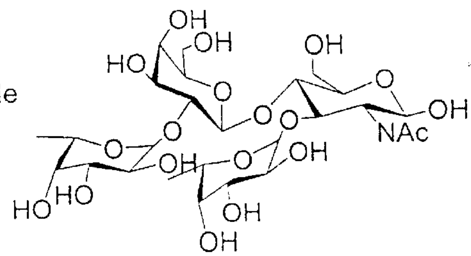 | 5400 ± 7000 |
| Sialyl Lewis A | 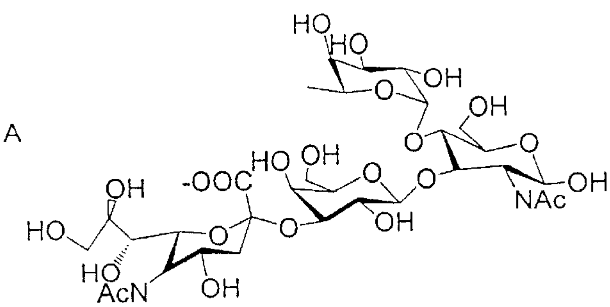 | 6100 ± 1000 |
| Sialyl Lewis X | 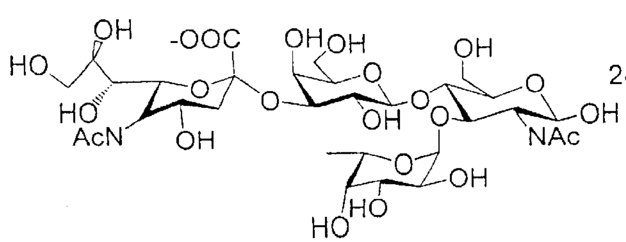 | 2800 ± 300 |

FIGURE 3B

| Competitor | Structure | $K_{dC}$, mM |
|---|---|---|
| LacNAc {Gal1-B-4GlcNAc} | 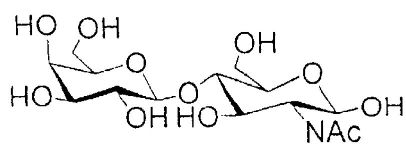 | 480 ± 250 |
| Sialyl-a-3LacNAc | 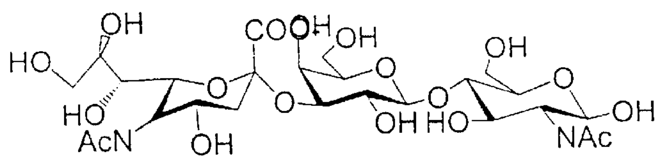 | 540 ± 170 |
| Sialyl-B-3LacNAc | 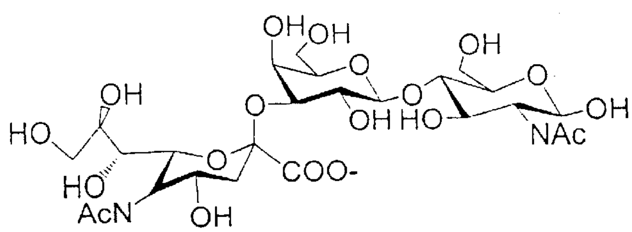 | 440 ± 200 |

FIGURE 3C

SEQUENCE LISTING

<160> NUMBER OF SEQ ID NOS: 4

<210> SEQ ID NO 1
<211> LENGTH: 33
<212> TYPE: DNA

-continued

```
<213> ORGANISM: Artificial Sequence
<220> FEATURE:
<223> OTHER INFORMATION: Description of Artificial Sequence: Nucleic
      acid ligand

<400> SEQUENCE: 1
cgggcgcgtt cttcgtggtt acttttagtc ccg                               33

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Nucleic
      acid ligand

<400> SEQUENCE: 2
gggccgtttc gggttacttt tagtccc                                      27

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Nucleic
      acid ligand
<220> FEATURE:
<221> NAME/KEY: modified_base
<222> LOCATION: (1)..(31)
<223> OTHER INFORMATION: The t at position 1 is 2'-NH2.  The u's and c's
      at positions 7, 9, 20, 21, 27, 28 and 29 are 2'-F.  The a's and g's
      at positions 10, 15, 17, 22 and 30 are 2'-O-methyl.
<220> FEATURE:
<221> NAME/KEY: modified_base
<222> LOCATION: (1)..(31)
<223> OTHER INFORMATION: The g at position 10 and the a at position 22
      have been modified with polyethylene glycol of 18 units.

<400> SEQUENCE: 3
tcaggcuacg cgtagagcau catgatccug t                                 31

<210> SEQ ID NO 4
<211> LENGTH: 97
<212> TYPE: RNA
<213> ORGANISM: Artificial Sequence
<220> FEATURE:
<223> OTHER INFORMATION: Description of Artificial Sequence: Nucleic
      acid ligand
<220> FEATURE:
<221> NAME/KEY: modified_base
<222> LOCATION: (1)..(97)
<223> OTHER INFORMATION: All u's and c's are 2'-aminopyrimidines

<400> SEQUENCE: 4
gggaaaagcg aaucauacac aagauugguc guacuggaca gagccguggu agagggauug  60
ggacaaagug ucagcuccgc cagagaccaa ccgagaa                           97
```

DETERMINING NON-NUCLEIC ACID MOLECULE BINDING TO TARGET BY COMPETITION WITH NUCLEIC ACID LIGAND

RELATED APPLICATIONS

This application is a continuation of U.S. application Ser. No. 09/246,641, filed Feb. 9, 1999, now U.S. Pat. No. 6,329,145 B1.

FIELD OF THE INVENTION

This invention is directed to a high throughput screening (HTS) method that uses aptamers to facilitate the identification of non-aptamer ligands, typically small molecules. Aptamers can be identified that bind to a wide variety of targets and can be used to identify small molecules that can compete with the aptamers for binding to the target.

BACKGROUND OF THE INVENTION

Drug discovery in most pharmaceutical companies is heavily focused on the identification of orally active compounds. High throughput screening (HTS) of appropriate libraries of compounds (generally small molecules) against validated targets constitutes one of the major activities in discovery research groups whose overall goal is to create and/or maintain a pipeline of new drug candidates. The development of HTS assays that allow efficient detection of active compounds from such libraries is thus a critically important component of drug discovery. With increasing numbers of both validated targets and compound libraries, HTS laboratories are under considerable pressure to find ways to increase throughput and lower cost. Assay development and validation is often one of the bottlenecks in this process (Fox et al., (November 1998) Drug Discovery & Development (Supplement to R&D Magazine) p. 32–37, incorporated by reference in its entirety).

Aptamers (also termed nucleic acid ligands) are structurally unique nucleic acids capable of binding other molecules (i.e., targets) with high affinity and specificity. Aptamers are derived from large random libraries by the SELEX process in which iterative rounds of affinity selection and amplification are used to identify sequences with specific binding properties. The SELEX process is described in more detail below. To date, aptamers that bind to small organic molecules, carbohydrates, amino acids, peptides and proteins have been identified, illustrating the multitude of binding specificities present in large collections of single stranded nucleic acid sequences (Gold, L., et al. (1995) Annu. Rev. Biochem. 64, 763–797). Aptamers bind to protein targets including growth factors, enzymes, receptors and structural proteins in a highly specific manner and with dissociation constants typically in the nanomolar (and sometimes picomolar) range. Given these unique binding properties, nuclease stabilized and appropriately formulated aptamers have substantial potential as therapeutics. For therapeutic uses, aptamers, like antibodies, are delivered parenterally because of their limited oral availability. The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. patent application Ser. No. 07/714,131, filed Jun. 10, 1991, entitled "Nucleic Acid Ligands," now U.S. Pat. No. 5,475,096, and U.S. patent application Ser. No. 07/931,473, filed Aug. 17, 1992, entitled "Methods for Identifying Nucleic Acid Ligands," now U.S. Pat. No. 5,270,163 (see also WO 91/19813), each of which is specifically incorporated by reference herein. Each of these applications, collectively referred to herein as the SELEX Patent Applications, describes a fundamentally novel method for making a nucleic acid ligand to any desired target molecule. The SELEX process provides a class of products which are referred to as aptamers or nucleic acid ligands, each ligand having a unique sequence, and which has the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

The SELEX method demonstrates that nucleic acids as chemical compounds can form a wide array of shapes, sizes and configurations, and are capable of a far broader repertoire of binding and other functions than those displayed by nucleic acids in biological systems. SELEX or SELEX-like processes can be used to identify nucleic acids which can facilitate any chosen reaction in a manner similar to that in which nucleic acid ligands can be identified for any given target. In theory, within a candidate mixture of approximately $10^{13}$ to $10^{18}$ nucleic acids, at least one nucleic acid exists with the appropriate shape to facilitate each of a broad variety of physical and chemical interactions.

The basic SELEX method has been modified to achieve a number of specific objectives. For example, U.S. patent application Ser. No. 07/960,093, filed Oct. 14, 1992, now abandoned, entitled "Method for Selecting Nucleic Acids on the Basis of Structure," describes the use of the SELEX process in conjunction with gel electrophoresis to select nucleic acid molecules with specific structural characteristics, such as bent DNA. U.S. patent application Ser. No. 08/123,935, filed Sep. 17, 1993, now abandoned, entitled "Photoselection of Nucleic Acid Ligands," describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now U.S. Pat. No. 5,580,737, describes a method for identifying highly specific nucleic acid ligands able to discriminate between closely related molecules, which can be non-peptidic, termed Counter-SELEX. U.S. patent application Ser. No. 08/143,564, filed Oct. 25, 1993, entitled "Systematic Evolution of Ligands by EXponential Enrichment: Solution SELEX," now U.S. Pat. No. 5,567,588, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," now abandoned (see U.S. Pat. No. 5,660,985), that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methl (2'-OMe). U.S. patent application Ser. No. 08/264,029, filed Jun. 22, 1994, now abandoned, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by EXponential Enrichment: Chimeric SELEX," now U.S. Pat. No. 5,637,459, and U.S. patent application Ser. No. 08/234,997, filed Apr. 28, 1994, entitled "Systematic Evolution of Ligands by EXponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled "Nucleic Acid Ligand Complexes." now U.S. Pat. No. 6,011,020. Each of the above described patent applications which describe modifications of the basic SELEX procedure are specifically incorporated by reference herein in their entirety.

SUMMARY OF THE INVENTION

The present invention describes the use of aptamers to facilitate the identification of non-aptamer ligands. More specifically, the present invention includes the use of aptamers in competition binding assays to rapidly identify compounds that are capable of displacing the aptamers from their targets. The affinities of competitor compounds can be calculated from the known affinity of the aptamer for its target and the competition profiles. The method is highly versatile and compatible with a variety of HTS platforms since aptamers, as chemically synthesized molecules, can be labeled in a variety of ways without compromising their binding affinity.

The method of the invention is illustrated with two protein targets: platelet derived growth factor (PDGF) and wheat germ agglutinin (WGA). For each protein, a small biased set of molecules is screened for their ability to displace the cognate aptamer: naphthalene sulfonic acid derivatives for PDGF and oligosaccharides for WGA. For both PDGF and WGA, best ligands can be identified readily. Furthermore, binding affinities of the competitors correlate with their activities in in vitro assays (infra, and in U.S. Pat. No. 5,780,222 issued Jul. 14, 1998).

BRIEF DESCRIPTION OF THE FIGURES

FIGS. 1A–C depicts the structures of small molecule oligoanion competitors used in the PDGF competition assay (dashed lines ($c_{2v}$) indicate a 2-fold axis of symmetry) along with the $K_{dc}$ values calculated from the competition profiles according to equations (1)–(3) and EC50 values derived from $^3$T-thymidine uptake assays.

FIGS. 3A–C depicts the structures of small molecule oligosaccharide competitors used in the WGA competition assay along with the $K_{dc}$ values calculated from the competition profiles according to equations (1)–(3).

DETAILED DESCRIPTION OF THE INVENTION

Figure 2A:
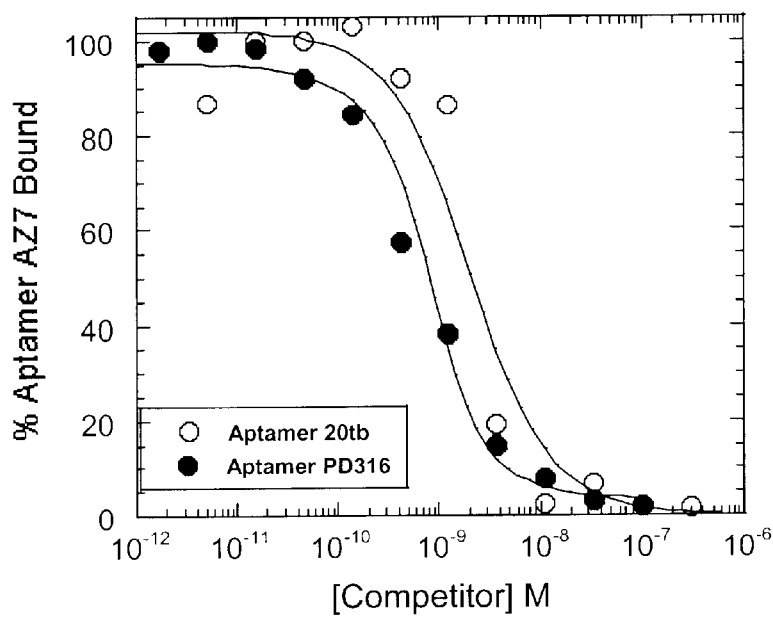
FIGS. 2A, 2B and 2C depict the competition profiles of the various small molecule oligoanion competitors for displacing the binding of a PDGF aptamer to PDGF.

The present invention describes the use of aptamers as a new class of reagents for high throughput screening (HTS) that may be used in conjunction with or in place of cell-based assays, receptor binding and other protein-protein interaction assays. The identification of aptamers to protein targets generally requires 5–15 rounds of the SELEX process to achieve affinities in the nanomolar range. A round of the SELEX process using manual protocols takes about one day, and considerably less than that using automated protocols such as those described in U.S. patent application 09/232,946, entitled "Method and Apparatus for the Automated Generation of Nucleic Acid Ligands", filed Jan. 19, 1999, which is incorporated herein in its entirety. Aptamer identification is thus rapid.

It is important to note that for use in competition assays described here, the affinity of aptamers for their targets need not be very high, since the affinity of first generation lead compounds will typically be considerably lower than that of an aptamer (e.g., in the micromolar range). For example, for the purposes of this invention it was useful to reduce the affinity of a previously identified PDGF aptamer (described in U.S. Pat. No. 5,723,594, entitled "High Affinity PDGF Nucleic Acid Ligands," issued Mar. 3, 1998, which is incorporated herein in its entirety) about 10-fold to facilitate the identification of competitors that bind PDGF with micromolar affinities. Lower affinity requirements may further speed up the identification of appropriate aptamers for competition assays. More generally, the affinities of aptamers and binding conditions (such as concentrations of the binding species) can be tuned to facilitate detection of ligands in a defined concentration range. Aptamers may be particularly useful for the identification of ligands to protein targets that do not have a known binding partner, such as orphan receptors.

The use of competition binding screens with aptamers (or any other ligands) does not guarantee that all compounds from a library that are capable of binding to the target will be identified, since the assay requires competitive displacement. To decrease the chance that active compounds may be missed, one can use more than one aptamer for the screens. It is important to note in this context, however, that in most cases, aptamers identified to protein targets generally compete with each other even when they belong to different sequence families or have different compositions (RNA, DNA or modified RNA). Nevertheless, given their size (typically 6–13 kDa), most aptamers are likely to cover a significant surface fraction of their protein targets which should reduce the problem of false negatives in competition assays. Furthermore, as illustrated with the WGA aptamers (described in U.S. Pat. No. 5,780,228 issued Jul. 14, 1998, which is incorporated herein in its entirety), aptamers that bind to specific sites on proteins can be selected provided that a ligand that binds to that site is available.

High affinity binding of aptamers for protein targets is typically encoded in sequences of 20–40 nucleotides. The efficient encoding of high affinity binding allows aptamers to be synthesized entirely chemically, e.g., by the solid phase phosphoramidite method. Aside from the advantage of being able to control batch-to-batch variability and lower reagent cost, chemical synthesis facilitates the incorporation of various non-nucleic acid functionalities into aptamers in a manner that does not disrupt their exquisite binding properties. Therefore, although radiolabeled aptamers are used in the examples herein, aptamers can be labeled in a variety of other ways (e.g., with light-absorbing, fluorescent or chemiluminescent moieties, biotin, etc.) that may be more suitable for some HTS applications.

Definitions

Various terms are used herein to refer to aspects of the present invention. To aid in the clarification of the description of the components of this invention, the following definitions are provided:

As used herein, "aptamer" or "nucleic acid ligand" is a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein, "non-aptamer ligands" or "non-nucleic acid molecule" is any molecule that is not an aptamer. Typically this term includes but is not limited to small molecules.

As used herein, "candidate mixture" is a mixture of nucleic acids of differing sequence from which to select a desired aptamer. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. The SELEX methodology is described in the SELEX Patent Applications.

"Target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation.

As used herein, "solid support" is defined as any surface to which molecules may be attached through either covalent or non-covalent bonds. This includes, but is not limited to, membranes, plastics, magnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces.

"Partitioning" means any process whereby aptamers bound to target molecules can be separated from nucleic acids not bound to target molecules. More broadly stated, partitioning allows for the separation of all the nucleic acids in a candidate mixture into at least two pools based on their relative affinity to the target molecule. Partitioning can be accomplished by various methods known in the art. Nucleic acid-protein pairs can be bound to nitrocellulose filters while unbound nucleic acids are not. Columns which specifically retain nucleic acid-target complexes can be used for partitioning. For example, oligonucleotides able to associate with a target molecule bound on a column allow use of column chromatography for separating and isolating the highest affinity nucleic acid ligands. Beads upon which target molecules are conjugated can also be used to partition nucleic acid ligands in a mixture. Surface plasmon resonance technology can be used to partition nucleic acids in a mixture by immobilizing a target on a sensor chip and flowing the mixture over the chip, wherein those nucleic acids having affinity for the target can be bound to the target, and the remaining nucleic acids can be washed away. Liquid-liquid partitioning can be used as well as filtration gel retardation, and density gradient centrifugation.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a certain amount of the nucleic acids in the candidate mixture are retained during partitioning.

4) Those nucleic acids selected during partitioning as having relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including protein targets wherein the protein is or is not a nucleic acid binding protein.

In the preferred embodiment of this invention, aptamers are used in conjunction with an existing HTS platform that allows inspection of multiple wells in an automated format. Any and all HTS platforms are contemplated for use in the present invention. For example, a target could be immobilized on a solid support and incubated with labeled aptamer. Any labeling method is contemplated by the present invention, including but not limited to radioactive, light-absorbing, fluorescent, chemiluminescent or other detectable moieties. A library of non-aptamer candidate molecules could then be tested for their ability to displace the aptamer from its target by measuring either the amount of labeled aptamer displaced or the amount of labeled aptamer remaining on the solid support. Alternatively, the aptamer could be immobilized on a solid support and incubated with a labeled target. A library of non-aptamer candidate molecules could then be tested for their ability to displace the labeled target as described above. Any known method for detecting the displaced aptamer is contemplated by the present invention, including but not limited to direct detection or amplified detection such as that described in U.S. application Ser. No. 09/157,206 filed Sep. 18, 1998, entitled "Homogenous Detection of a Target Through Nucleic Acid Ligand-Ligand Beacon Interaction," now U.S. Pat. No. 5,989,823, which is incorporated herein in its entirety by reference.

In certain embodiments, the method can take place in solution with the aptamer and small molecule competing simultaneously.

EXAMPLES

The Examples provided below are illustrative embodiments of the invention. They are not to be taken as limiting the scope of the invention.

Example One

Material and Methods

Materials

Human recombinant platelet derived growth factor, BB isoform (PDGF BB) was purchased from R&D Systems (Minneapolis, Minn.) as a carrier free lyophilized powder. Wheat Germ (*Triticum vulgare*) Agglutinin (WGA) was from EY laboratories (San Mateo, Calif.).

Oligonucleotides were synthesized using an Applied Biosystems Model 394 oligonucleotide synthesizer according to optimized protocols. PDGF aptamer 20 ta is a

```
synthetic 33-mer DNA oligo sequence:
5'CGGGCGCGTTCTTCGTGGTTACTTTTAGTCCCG, (SEQ ID NO: 1)

aptamer 20tb is a synthetic 27-mer DNA
oligo sequence:
5'GGGCCGTTTCGGGTTACTTTTAGTCCC         (SEQ ID NO: 2)
``` and aptamer PD316 is a synthetic oligo containing some modified (2'F and 2'O-methyl, italic and bold letters, respectively) bases, and an 18-atom PEG spacer replacing some bases, to increase serum stability, of sequence:

5'T$_{NH2}$CAGGCUACG[PEG$_{18}$]CGTAGAGCAUCA[PEG$_{18}$]TGATCCUG-3'3'T (SEQ ID NO: 3).

WGA aptamer 11.20 is a 98-mer RNA transcript with 2'aminopyrimidine bases of sequence:

(SEQ ID NO: 4)
5'GGGAAAAGCGAAUCAUACACAAGAUUGGUCGUACUGGACAGAGCCGUG
GUAGAGGGAUUGGGACAAAGUGUCAGCUCCGCCAGAGACCAACCGAGAA.

PDGF aptamers were previously described in U.S. Pat. No. 5,723,594 issued Mar. 3, 1998. WGA aptamers were previously described in U.S. Pat. No. 5,780,228 issued Jul. 14, 1998.

Oligoanions used in the PDGF aptamer competition assay were: Evans blue, trypan Blue, amaranth, sulfonazo III, New Coccine, myoinositol hexasulfate, SPADNS (2-(4-sulfophenylazo)-1,8-dihydroxy-3,6-naphthalene disulfonic acid), calcion, and azocarmine B from Aldrich (Milwaukee, Wis.); NTSA (naphthalene 1,3,6-trisulfonic acid) from Fluka, suramin from Calbiochem (La Jolla, Calif.), and sucrose octasulfate from Toronto Research Chemicals (Toronto, Canada).

Oligosaccharides used in the WGA aptamer competition assay were: N-acetyl-D-glucosamine (GlcNAc) from Sigma (St. Louis, Mo.); N,N'-diacetylchitobiose (GlcNAc)$_2$, N,N', N"-triacetylchitotriose (GlcNAc)$_3$, N,N',N",N'"-tetraacetyltetraose (GlcNAc)$_4$, galactose 1-β-3(fucose-α-4) glucosamine (Lewis A trisaccharide), galactose 1-β-4 (fucose 1-α-3)glucosamine (Lewis X trisaccharide), fucosel-α-2 galactosel-β-4(fucose 1-α-3)glucosamine (Lewis Y tetrasaccharide), Sialyl Lewis A, Sialyl Lewis X, fucosel-α-4glucosamine, fucosel-α-glucosamine, N-acetyl-lactosamine (LacNAc), 3'α-Sialyl-N-acetyllactosamine (α-Sialyl-LacNAc), 3'β-Sialyl-N-acetyllactosamine (β-Sialyl-LacNAc), from Toronto Research Chemicals (Toronto, Canada).

Methods

Small Molecule/Aptamer Competition Assays

Small molecule oligoanions were screened for their ability to compete with PDGF aptamer 20tb for binding to the PDGF-BB protein. The small molecule (or cold 20tb) competitors at varying concentrations were mixed with the 5'-$^{32}$P end-labeled 20tb ligand at room temperature. PDGF was then added to the mixture and allowed to equilibrate for 45 minutes at room temperature followed by 15 minutes at 37° C. The competition mixtures (90 μL volume) all had $^{32}$P end-labeled 20tb at 1.16 nM, PDGF-BB at 1 nM and were in 25 mM Hepes, 137 mM NaCl, 2.7 mM KCl, 1 mM MgCl$_2$, 1 mM CaCl$_2$, 0.067% human serum albumin (HSA), at pH 7.4 (HBSMC). Aptamer bound to PDGF was separated from free aptamer by filtration through pre-washed 0.45 μM nitrocellulose membrane filters (Millipore; Bedford, Mass.). Filters were washed with 5 mL HBSMC at room temperature. The filters were placed in tubes with scintillant and the radioactivity counted to quantitate the fraction of $^{32}$P end-labeled 20tb bound at each competitor concentration.

Small molecule oligosaccharides were screened for their ability to compete with WGA aptamer 11.20 for binding to wheat germ agglutinin protein. The small molecule (or cold 11.20) competitors at varying concentrations were mixed with the 5'-32P end-labeled 11.20 ligand at room temperature. Then WGA was added to the mixture and allowed to equilibrate for 60 minutes at room temperature. The competition mixtures (90 μL volume) all had 32P end-labeled 11.20 at 10 nM, WGA at 10 nM and were in 25 mM Hepes, 137 mM NaCl, 2.7 mM KCl, 1 mM MgCl2, 1 mM CaCl2, 0.067% human serum albumin (HSA), at pH 7.4 (HBSMC). Aptamer bound to WGA was separated from free aptamer by filtration through pre-washed 0.45 μM nitrocellulose membrane filters. Filters were washed with 5 mL HBSMC at room temperature. The filters were placed in tubes with scintillant and the radioactivity counted to quantitate the fraction of 32P end-labeled 11.20 bound at each competitor concentration.

Analysis of Competition Data

Competition experiments were analyzed by the following equation to determine the concentration of free protein, $[P_F]$, as a function of the total concentration of competitor added, $[C_T]$:

$$[P_F]=[P_T]/(1+K_{dR}[R_T]/(1+K_{dR}[P_F])+K_{dC}[C_T]/(1+K_{dC}[P_F])) \quad (1)$$

where $K_{dR}$ is the binding constant of species R to the protein (assuming 1:1 stoichiometry) and $K_{dC}$ is the binding constant of species C, the competitor, to the protein (assuming 1:1 stoichiometry). Equation (1) was solved to self-consistency of $[P_F]$ to a precision of $1\times10^{-15}$. Using these values of $[P_F]$, the concentration of protein-ligand complex [PR] as a function of $[C_T]$ was determined by the following equation:

$$[PR]=K_{dR}[R_T][P_F](1+K_{dC}[PF]) \quad (2)$$

Since the experimental data are expressed as %[PR], the calculated concentration of [PR] was normalized by [PR$_0$], the [PR] in the absence of the competitor. [PR$_0$] was obtained by solving equation (1) where $[C_T]=0$. The maximum (M) and minimum (B) %[PR] were allowed to float during the analysis as shown in the following equation:

$$\%[PR]=[PR]/[PR_0](M-B)+B \quad (3)$$

A non-linear least-squares fitting procedure was used as described by Bates and Watts (Bates, D. M. and Watts, D. G. 1988 in Non-Linear Regression Analysis and its Applications, D. M. Bates and D. G. Watts editors, John Wiley & Sons, NY, N.Y.). The program used was originally written in C program language by Dominic Zichi and Brenda Javornic, NeXstar Pharmaceuticals, Inc. The data were fit to equations (1) to (3) to obtain best fit parameters for KdC, M and B as a function of [CT] while leaving KdR and [PT] constant.

Inhibition of PDGF Stimulated [$^3$H]-thymidine Incorporation

A10 rat smooth muscle cells were plated in 96 well tissue culture plates at 7–8×10$^3$ per well in 100 μL DME+4.5 g/L glucose+HEPES+0.1% FBS and starved for about 20 hours. Aptamers or small molecule oligoanions were titrated across the 96 well plate in triplicate wells from 1 mM to 0.3 μM by 1:3 dilution steps for the oligoanions, and from 1 μM to 0.3 nM by 1:3 steps for the aptamers. Immediately, PDGF-BB was added to 10 ng/ml to all wells except the unstimulated controls. Positive controls had only PDGF-BB, no other compounds. After 6 hours at 37° C. in 5% CO$_2$, $^3$H-thymidine was added (0.25 μCi per well) and incubated for another 24 hours. Cells were lysed in 1% triton-X 100 for 20–30 minutes on a slow shaker at room temperature, then harvested onto 96 well glass fiber filter plates (Packard) and dried. Scintillant was added and incorporated $^3$H-thymidine radioactivity counted. EC50 values for inhibition of PDGF-BB-induced $^3$H-thymidine uptake were obtained by fitting the data to the nonlinear regression with variable slope model of the GraphPad Prism computer program (GraphPad Software).

Example Two
PDGF Aptamer Competition Assay

For the PDGF competition assay, a DNA PDGF aptamer sequence identified previously was used. The aptamer and methods used herein are described in detail in Example One. Aptamers obtained in this experiment bind preferentially to the B-chain of PDGF in a manner that inhibits receptor binding and PDGF-BB-induced DNA synthesis in vitro. Using photo-crosslinking experiments, it has been shown that a specific nucleotide in the aptamer interacts with phenylalanine-84 of the PDGF B-chain which is located near the region of PDGF know to be involved in receptor binding (Green, L. S. et al. (1996) Biochemistry 35, 14413–24). To facilitate detection of competitors in the micromolar range, the affinity of the PDGF aptamer 20ta ($K_d$=50 pM), a 33-mer, was deliberately reduced about 10-fold by additional truncations. Thus, the aptamer used for competition binding experiments, 20tb, is a 27-mer that binds to PDGF-BB with a $K_d$ of 0.5 nM.

Figure 2B:
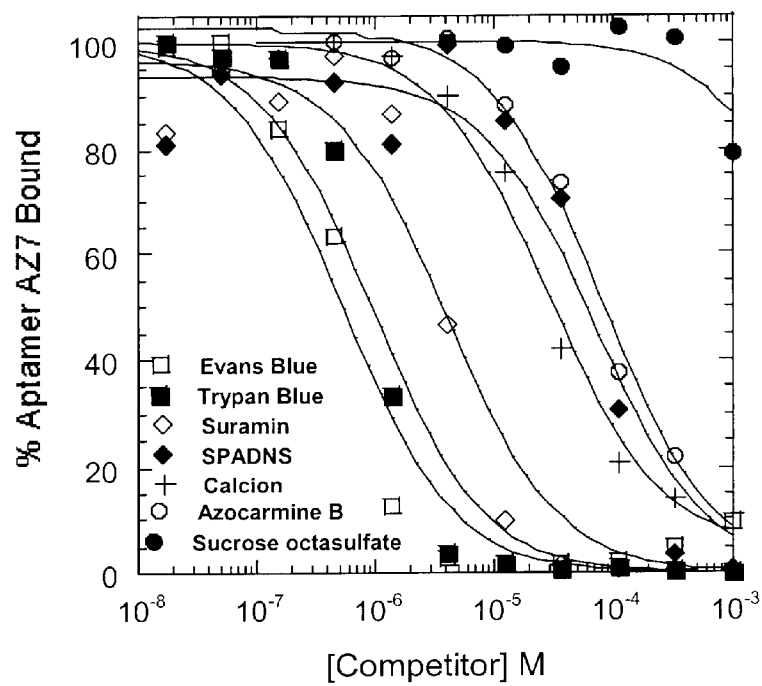
Figure 2C:
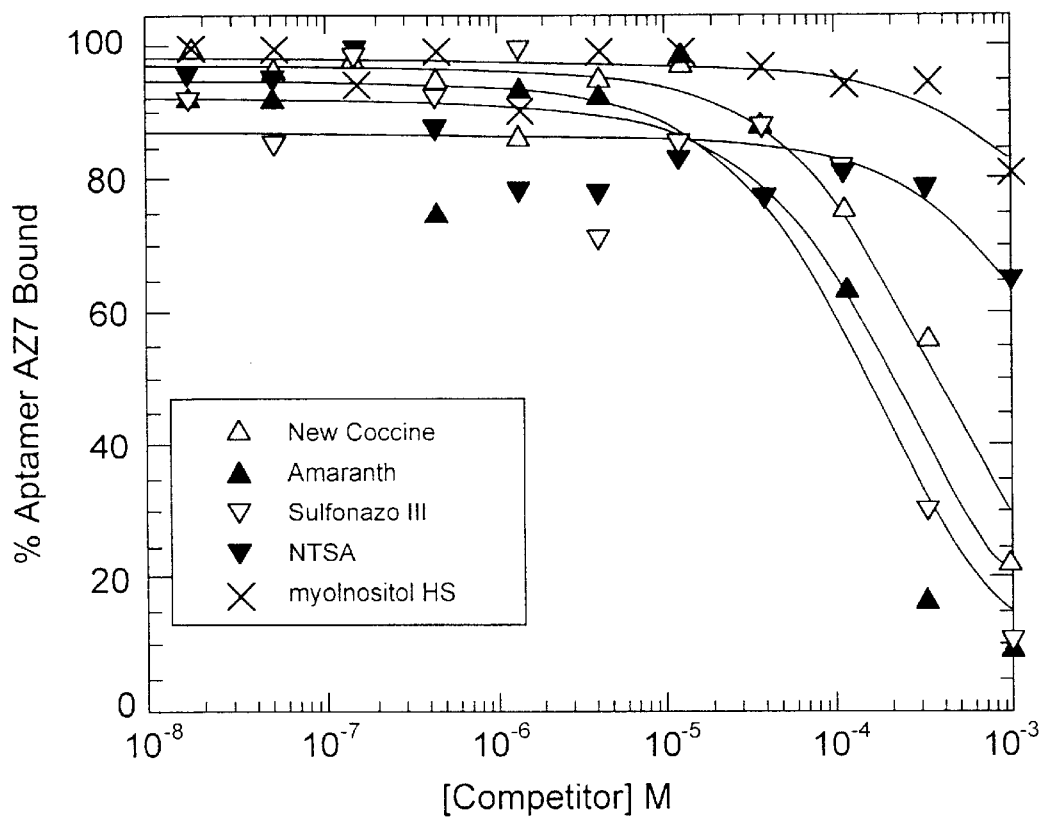
Figure 4A:
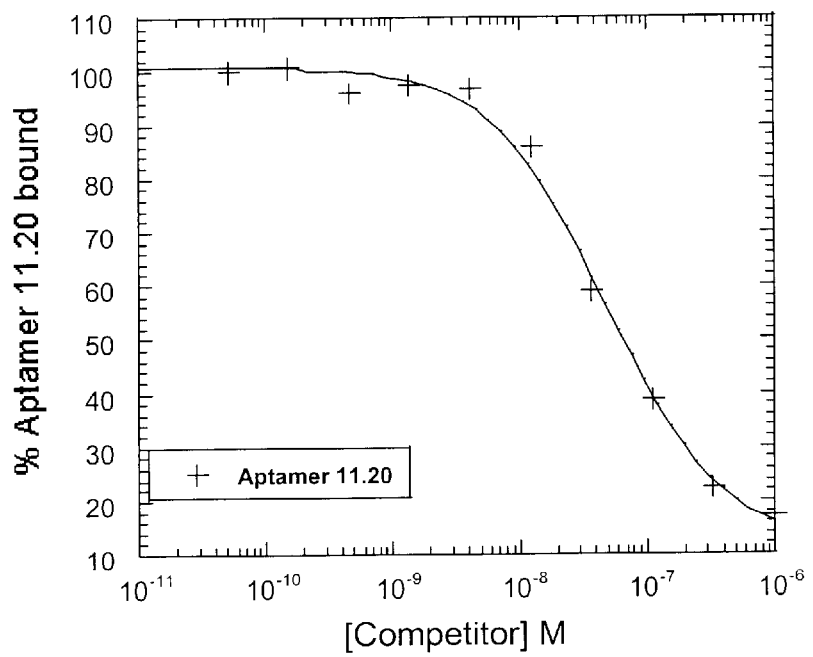
FIGS. 4A, 4B, 4C and 4D depict the competition profiles of the various small molecule oligosaccharide competitors for displacing the binding of the WGA aptamer to WGA.
Figure 4B:
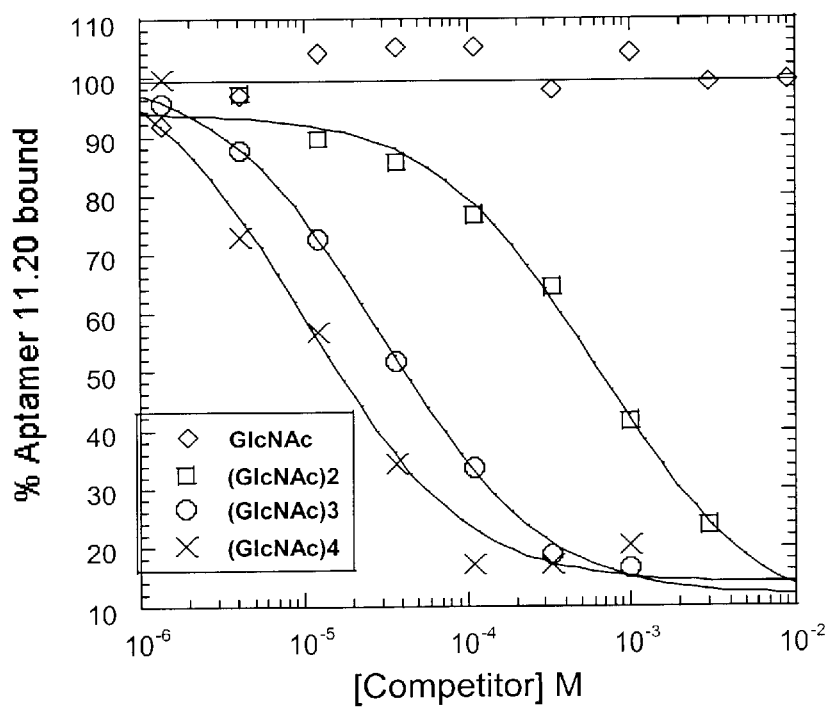
Figure 4C:
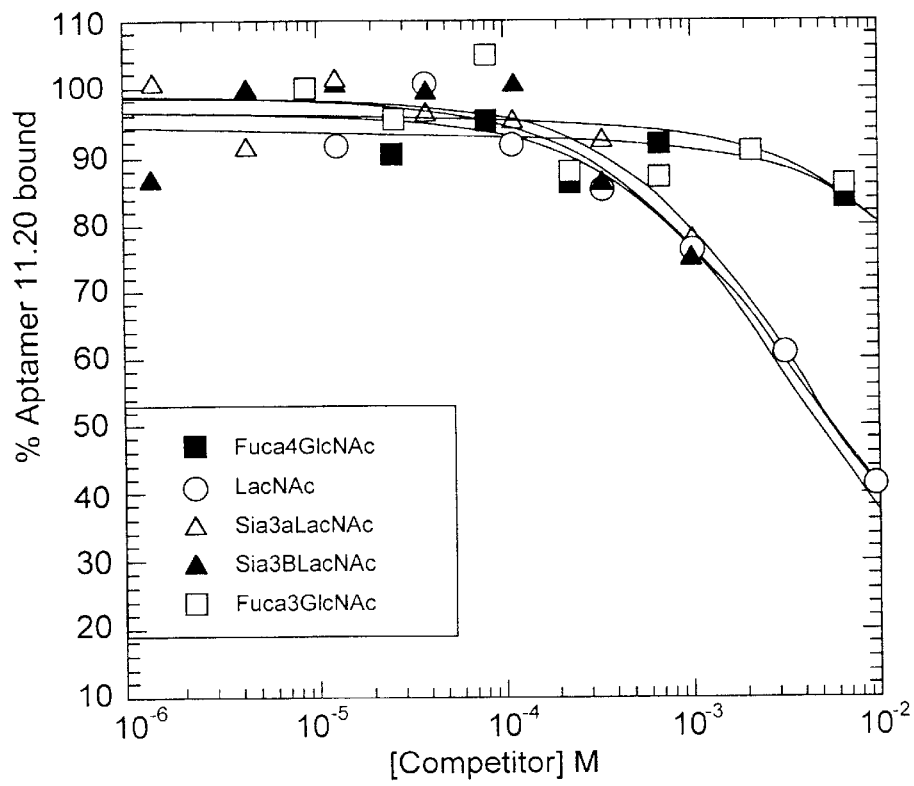
Figure 4D:
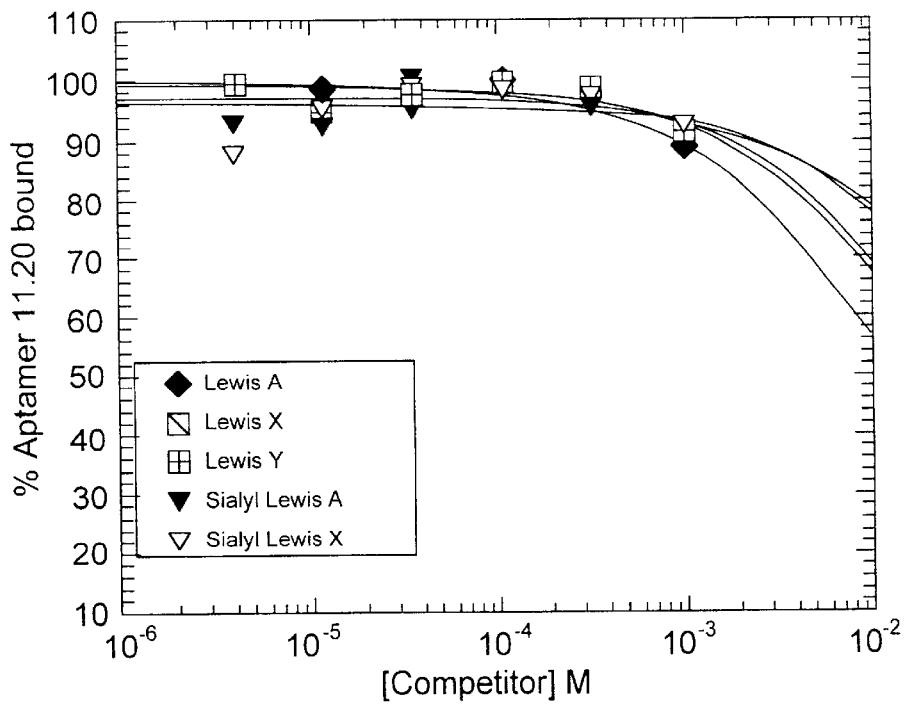

A panel of oligoanions, mostly in the naphthalene sulfonic acid class, were screened for their ability to displace a $^{32}$P-radiolabeled aptamer (20tb) from PDGF-BB. These compounds were chosen because suramin and several other members of this family inhibit the binding of PDGF to cells that express the PDGF receptor (Garrett, J. S. et at. (1984) PNAS 81 7466–7470; Powis, G. et at. (1992) Cancer Chemother. Pharmacol 31 223–228). Since the PDGF aptamer also inhibits receptor binding (and with considerably greater potency), it was reasonable to expect that suramin and the aptamer bind to PDGF in a mutually exclusive manner. This was a deliberately biased library and was not intended to approximate any conventional or combinatorial libraries but simply to demonstrate that such competition assays are feasible. A nitrocellulose filter binding method was used to separate bound from unbound aptamer. Structures of competitors used in this competition assay are shown in FIGS. 1A–C along with the $K_{dc}$ values calculated form the competition profiles (FIG. 2) according to equations (1)–(3) (Experimental Methods). For all competition experiments, the concentration of the $^{32}$P end-labeled 20tb aptamer and PDGF-BB was 1.16 nM and 1.0 nM, respectively. Binding reactions were done at 37° C. and the time of incubations was at least 60 mm to insure that the equilibrium was established ($t_{1/2}$ of dissociation for the aptamer from PDGF-BB is about 2 mm). Fast dissociation kinetics are clearly advantageous in these assays since they reduce the length of time required to reach equilibrium.

Among the eleven compounds in the naphthalene sulfonic acid derivatives class, there is clearly a range of affinities for PDGF. Suramin, a hexaanion, is actually not the best ligand for PDGF-BB. Inspection of this set clearly suggests that the placement of the sulfonic acid groups (or anions in general) in space is a strong determinant of binding affinity. For example, naphthalene 1,3,6-trisulfonic acid binds with a $K_{dc}$ of 870 μM whereas SPADNS (another trianion with certain structural similarity to naphthalene 1,3,6-trisulfonic acid) binds with a KdC of 19 μM. The total number of negative charges seems to be less important than their appropriate placement (compare suramin, a hexaanion with myoinositol hexasulfate, also a hexaanion or sucrose octasulfate, an octaanion).

Example Three
Effect of Ligands on PDGF-induced $^3$T-thymidine Synthesis in A10 Rat Smooth Muscle Cells The same panel of small molecule oligoanions was tested for its effect on PDGF-BB-induced $^3$T-thymidine incorporation in A10 rat smooth muscle cells as described in Example one. The EC50 values for all compounds tested were calculated as described in Example one and are listed in FIGS. 1A–C.

Example Four
Wheat Germ Agglutinin Aptamer Competition Assay

For the WGA competition assay, a 2'-aminopyrimidine RNA aptamer 11.20 identified previously was used. The aptamer and methods used herein are described in detail in Example One. Aptamer 11.20 was selected by incubating a randomized nucleic acid library with WGA, removing the unbound molecules and then displacing the aptamers bound to a specific site with a competitor, $(GlcNAc)_3$. Thus, unlike the PDGF aptamer, which was selected for high affinity binding anywhere on the protein, the WGA aptamers were selected for binding to a specific site, the $(GlcNAc)_3$ binding site. Aptamer 11.20 and related aptamers isolated by this procedure potently inhibited WGA-mediated agglutination of sheep erythrocytes. Not surprisingly, 11.20 and related aptamers could be displaced with $(GlcNAc)_3$ (as described in U.S. Pat. No. 5,780,228 issued Jul. 14, 1998).

A group of carbohydrates related to $GlcNAc_3$ were tested for their ability to displace radiolabeled 11.20 from WGA. As with PDGF, nitrocellulose filter binding assay was used to separate bound from unbound aptamer. Structures of competitors used in this assay are shown in FIGS. 3A–C along with the $K_{dc}$ values calculated from the competition profiles (FIGS. 4A–D) according to equations (1)–(3). Binding conditions are described in detail in Example One.

Among the carbohydrates tested there is a wide range of affinities for WGA. The best ligands were $(GlcNAc)_4$, $(GlcNAc)_3$, and $(GlcNAc)_2$, in that order (FIGS. 3 and 4). This result is in agreement with previous observations (Goldstein, I. J. and Poretz, R. D. (1986) In: The Lectins. Properties, functions, and applications in biology and medicine, Academic Press, NY, pp 233–247). GlcNAc was not a competitor in this concentration range. The ability of $(GlcNAc)_3$ and GlcNAc to inhibit WGA-mediated agglutination was tested previously (see U.S. Pat. No. 5,780,228 issued Jul. 14, 1998) (18.5 μM and 800 μM of the two compounds, respectively, were required to completely inhibit agglutination). Thus, for a subset of carbohydrates tested in the competition assay, $K_{dc}$ values correlate with inhibitory potency in a functional assay.

What is claimed is:

1. A method for determining whether at least one non-nucleic acid molecule from a library of candidate non-nucleic acid molecules binds to a target, wherein said non-nucleic acid molecule has an affinity for said target within a defined concentration range, comprising:
   a) providing a first nucleic acid ligand of said target, said nucleic acid ligand having a specific binding affinity for said target;
   b) modifying said first nucleic acid ligand of said target to yield a second nucleic acid ligand having a reduced binding affinity for said target relative to said first nucleic acid ligand;
   c) immobilizing a target to a solid support;
   d) contacting said second nucleic acid ligand with said target wherein binding of the second nucleic acid ligand to the target occurs to form a complex;
   e) adding a non-nucleic acid molecule to the complex wherein the non-nucleic acid molecule competes with the second nucleic acid ligand for binding to the target and disrupts the complex and liberates the second nucleic acid ligand; and f) detecting the liberation of the second nucleic acid ligand thereby determining that said non-nucleic acid molecule binds to said target with an affinity within said defined concentration range.

2. The method of claim 1 wherein said first nucleic acid is identified by the method comprising:
   i) preparing a candidate mixture of nucleic acids;
   ii) contacting the candidate mixture of nucleic acids with said target, wherein nucleic acids having an increased affinity to said target relative to the candidate mixture may be partitioned from the remainder of the candidate mixture;
   iii) partitioning the increased affinity nucleic acids from the remainder of the candidate mixture; and
   iv) amplifying the increased affinity nucleic acids to yield a mixture of nucleic acids enriched for nucleic acids with relatively higher affinity and specificity for binding to said target, whereby a nucleic acid ligand may be identified for binding to said target.

3. The method of claim 2 wherein said second nucleic acid ligand is produced by truncating said first nucleic acid ligand.

4. The method of claim 2 wherein said second nucleic acid ligand comprises a label, and wherein the liberation of the second nucleic acid ligand is detected by monitoring the presence of said label on said solid support.

5. The method of claim 4 wherein said label is selected from the group consisting of radiolabels, fluorophores, and chemiluminescent compounds.

6. The method of claim 2 wherein said non-nucleic acid molecule is a small molecule.

7. A method for determining whether at least one non-nucleic acid molecule from a library of candidate non-nucleic acid molecules binds to a target, wherein said non-nucleic acid molecule has an affinity for said target within a defined concentration range, comprising:
   a) providing a first nucleic acid ligand of said target, said first nucleic acid ligand having a specific binding affinity for said target;
   b) modifying said first nucleic acid ligand of said target to yield a second nucleic acid ligand having a reduced binding affinity for said target relative to said first nucleic acid ligand;
   c) immobilizing said second nucleic acid ligand to a solid support;
   d) contacting said second nucleic acid ligand with a target wherein binding of the second nucleic acid ligand to the target occurs to form a complex;
   e) adding a non-nucleic acid molecule to the complex wherein the non-nucleic acid molecule competes with the second nucleic acid ligand for binding to the target and disrupts the complex and liberates the target; and
   f) detecting the liberation of target thereby determining that said non-nucleic acid molecule binds to said target within said defined concentration range.

8. The method of claim 7 wherein said first nucleic acid ligand is identified by the method comprising:
   i) preparing a candidate mixture of nucleic acids;
   ii) contacting the candidate mixture of nucleic acids with said target, wherein nucleic acids having an increased affinity to said target relative to the candidate mixture may be partitioned from the remainder of the candidate mixture;
   iii) partitioning the increased affinity nucleic acids from the remainder of the candidate mixture; and
   iv) amplifying the increased affinity nucleic acids to yield a mixture of nucleic acids enriched for nucleic acids with relatively higher affinity and specificity for binding to said target, whereby a nucleic acid ligand may be identified.

9. The method of claim 7 wherein said second nucleic acid ligand is produced by truncating said first nucleic acid ligand.

10. The method of claim 7 wherein said target comprises a label, and wherein the liberation of the target is detected by monitoring the presence of said label on said solid support.

11. The method of claim 7 wherein said label is selected from the group consisting of radiolabels, fluorophores, and chemiluminescent compounds.

12. The method of claim 7 wherein said non-nucleic acid molecule is a small molecule.

* * * * *